United States Patent
Chen et al.

(10) Patent No.: US 10,324,056 B2
(45) Date of Patent: Jun. 18, 2019

(54) MOISTURE DETECTION AND INGRESSION MONITORING SYSTEMS AND METHODS OF MANUFACTURE

(71) Applicant: INTERNATIONAL BUSINESS MACHINES CORPORATION, Armonk, NY (US)

(72) Inventors: Fen Chen, Williston, VT (US); Jeffrey P. Gambino, Gresham, OR (US); Carole D. Graas, Jericho, VT (US); Wen Liu, Essex Junction, VT (US); Prakash Periasamy, Essex Junction, VT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/107,449

(22) Filed: Aug. 21, 2018

(65) Prior Publication Data
US 2018/0356358 A1    Dec. 13, 2018

Related U.S. Application Data

(63) Continuation of application No. 14/706,322, filed on May 7, 2015, now Pat. No. 10,126,260.

(51) Int. Cl.
*G01N 27/22* (2006.01)
*G01R 27/26* (2006.01)
(Continued)

(52) U.S. Cl.
CPC ....... *G01N 27/223* (2013.01); *G01R 27/2605* (2013.01); *G01D 5/24* (2013.01); *H03K 17/955* (2013.01)

(58) Field of Classification Search
CPC .... G01N 27/223; G01N 27/225; G01N 22/04; G01R 31/2856; G01R 27/048; G01R 27/26; G01R 27/2605; G01R 27/2607; H01L 22/34; G01D 5/24; G01D 5/241; G01D 5/2412; G01D 5/2417; G06K 9/0002; G06F 3/0414; G01L 1/146; H03K 17/955
(Continued)

(56) References Cited

U.S. PATENT DOCUMENTS

| | | | |
|---|---|---|---|
| 4,272,986 A | 6/1981 | Lowry et al. | |
| 4,775,831 A | 10/1988 | Annamalai | |

(Continued)

OTHER PUBLICATIONS

List of IBM Patents or Patent Applications Treated as Related 1 page.

(Continued)

*Primary Examiner* — Hoai-An D. Nguyen
(74) *Attorney, Agent, or Firm* — Steven Meyers; Andrew M. Calderon; Roberts Mlotkowski Safran Cole & Calderon, P.C.

(57) ABSTRACT

Moisture detection and ingression monitoring systems and methods of manufacture are provided. The moisture detection structure includes chip edge sealing structures including at least one electrode forming a capacitor structured to detect moisture ingress within an integrated circuit. The at least one electrode and a second electrode of the capacitor is biased to ground and to a moisture detection circuit or vice versa, respectively.

9 Claims, 6 Drawing Sheets

(51) Int. Cl.
*G01D 5/24* (2006.01)
*H03K 17/955* (2006.01)

(58) Field of Classification Search
USPC ....... 324/600, 649, 658, 663, 664, 665, 686, 324/688, 689, 694; 702/47, 51, 52; 73/24.04, 25.04, 29.01, 73, 74
See application file for complete search history.

(56) References Cited

U.S. PATENT DOCUMENTS

| | | | |
|---|---|---|---|
| 6,022,791 | A | 2/2000 | Cook et al. |
| 6,261,945 | B1 | 7/2001 | Nye, III et al. |
| 6,366,209 | B2 | 4/2002 | Dishongh et al. |
| 6,833,720 | B1 | 12/2004 | Daubenspeck et al. |
| 7,098,676 | B2 | 8/2006 | Landers et al. |
| 7,795,615 | B2 | 9/2010 | Goebel et al. |
| 7,893,459 | B2 | 2/2011 | Wang et al. |
| 7,955,952 | B2 | 6/2011 | Liu et al. |
| 7,994,613 | B2 | 8/2011 | Jung |
| 8,274,080 | B2 | 9/2012 | Han |
| 8,395,241 | B2 | 3/2013 | Yang et al. |
| 8,604,618 | B2 | 12/2013 | Cooney, III et al. |
| 8,674,710 | B2 | 3/2014 | Satake et al. |
| 8,779,548 | B2 | 7/2014 | Ponomarev et al. |
| 10,006,392 | B2 * | 6/2018 | Hoshika ............... F02D 41/18 |
| 10,036,657 | B2 * | 7/2018 | Reindl .................. G01D 5/24 |
| 10,075,163 | B2 * | 9/2018 | Nishiyama ............ E05B 1/0053 |
| 10,126,260 | B2 | 11/2018 | Chen et al. |
| 2008/0191716 | A1 | 8/2008 | Chen et al. |
| 2009/0107220 | A1 | 4/2009 | Chen et al. |
| 2014/0038390 | A1 | 2/2014 | Yang et al. |
| 2016/0327502 | A1 | 11/2016 | Chen et al. |
| 2018/0356358 | A1 | 12/2018 | Chen et al. |
| 2018/0356359 | A1 | 12/2018 | Chen et al. |

OTHER PUBLICATIONS

Specification and Drawungs for U.S. Appl. No. 16/107,544, Title "Moisture Detection and Ingression Monitoring Systems and Methods of Manufacture", filed Aug. 21, 2018, 27 pages.

Office Action in the related U.S. Appl. No. 16/107,544 dated Sep. 20, 2018, 12 pages.

List of IBM Patents or Patent Applications Treated as Related dated Apr. 30, 2019, 1 page.

Specification and Drawings in the related U.S. Appl. No. 16/394,436, Titled "Moisture Detection and Ingression Monitoring Systems and Methods of Manufacture", filed Apr. 23, 2019, 26 pages.

Specification and Drawings in the related U.S. Appl. No. 16/392,055, Titled "Moisture Detection and Ingression Monitoring Systems and Methods of Manufacture", filed Apr. 23, 2019, 26 pages.

Notice of Allowance in the related U.S. Appl. No. 16/107,544 dated Jan. 24, 2019, 8 pages.

* cited by examiner

MOISTURE DETECTION AND INGRESSION MONITORING SYSTEMS AND METHODS OF MANUFACTURE

FIELD OF THE INVENTION

The invention relates to semiconductor structures and, more particularly, to moisture detection and ingression monitoring systems and methods of manufacture.

BACKGROUND

Moisture greatly impacts integrated circuit reliability and performance. For example, moisture ingression during chip operational lifetime increases chip functional failure, particularly as technology scales. For example, capacitance shift due to moisture ingression (k value increases) will negatively impact performance (e.g., RC delay). Moreover, low-k interlevel dielectric (ILD) TDDB failure times, voltage acceleration, and temperature acceleration all degrade significantly with the ingress of moisture within an integrated circuit. These failures can become even more pronounced in integrated circuit designs in smaller technology nodes which do not take into consideration an increased likelihood of chip edge seal breakage due to high temperature swings or high mechanical stress generated by low-k ILD integration and high density circuit layouts.

SUMMARY

In an aspect of the invention, a moisture detection structure comprises chip edge sealing structures comprising at least one electrode forming a capacitor structured to detect moisture ingress within an integrated circuit. The at least one electrode and a second electrode of the capacitor is biased to ground and to a moisture detection circuit or vice versa, respectively.

In an aspect of the invention, a moisture detection structure comprises at least one metal structure surrounding one or more devices of an integrated circuit. The at least one metal structure includes a plurality of metal wiring layers connected together with via interconnects and having at least one electrode formed from a metal wiring layer of the metal wiring layers and which with a second electrode forms a capacitor structured to detect moisture ingress.

In an aspect of the invention, a method comprises: at an initial power up of an integrated circuit: measuring a value of Vc; converting the measured value to digital format; and saving the measured value as an initial value; and during operation of the integrated circuit: measuring the value of Vc; if the value of Vc is higher than a threshold voltage, then an output is at logic high and is normal; and if the value of Vc is lower than the threshold voltage, the output is at the logic low and a latch is triggered and an alarm is sent indicating that there is moisture.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

The invention relates to semiconductor structures and, more particularly, to moisture detection and ingression monitoring systems and methods of manufacture. More specifically, the present invention is directed to structures comprising an on-chip crackstop/guardring with moisture detection and moisture ingression monitoring functions and methods of manufacture. Advantageously, the on-chip moisture detection and moisture ingression monitoring structures provide on-chip real-time moisture warning ingression and detection functions, which detect moisture during chip packaging and chip field operation due to, e.g., chip crackstops/edge seals being compromised.

In more specific embodiments, the on-chip moisture detection and moisture ingression monitoring structures and methods of manufacture described herein provide a simple implementation with no extra manufacturing steps with existing processes. The on-chip moisture detection and moisture ingression monitoring structures comprise a capacitor that surrounds an electronic chip. The capacitor comprises plates formed by a guardring or crackstop with interlevel dielectrics formed between the plates. The capacitor is operatively coupled to an electronic circuit, wherein the electronic circuit detects a difference in capacitance of the capacitor corresponding to moisture ingress into the electronic chip.

Moreover, the on-chip moisture detection and moisture ingression monitoring structures can monitor moisture both vertically and horizontally at any metal levels (e.g., 3D implementation). For example, the on-chip moisture detection and moisture ingression monitoring structures comprise active guardrings/crackstops integrated with moisture sensing capability for a real-time 360 degree on chip moisture detection.

The moisture detection and ingression monitoring systems of the present invention can be manufactured in a number of ways using a number of different tools. In general, though, the methodologies and tools are used to form structures with dimensions in the micrometer and nanometer scale. The methodologies, i.e., technologies, employed to manufacture the moisture detection and ingression monitoring systems have been adopted from integrated circuit (IC) technology. For example, the structures of the present invention are built on wafers and are realized in films of material patterned by photolithographic processes on the top of a wafer. In particular, the fabrication of the moisture detection and ingression monitoring systems uses three basic building blocks: (i) deposition of thin films of material on a substrate, (ii) applying a patterned mask on top of the films by photolithographic imaging, and (iii) etching the films selectively to the mask.

Figure 1:
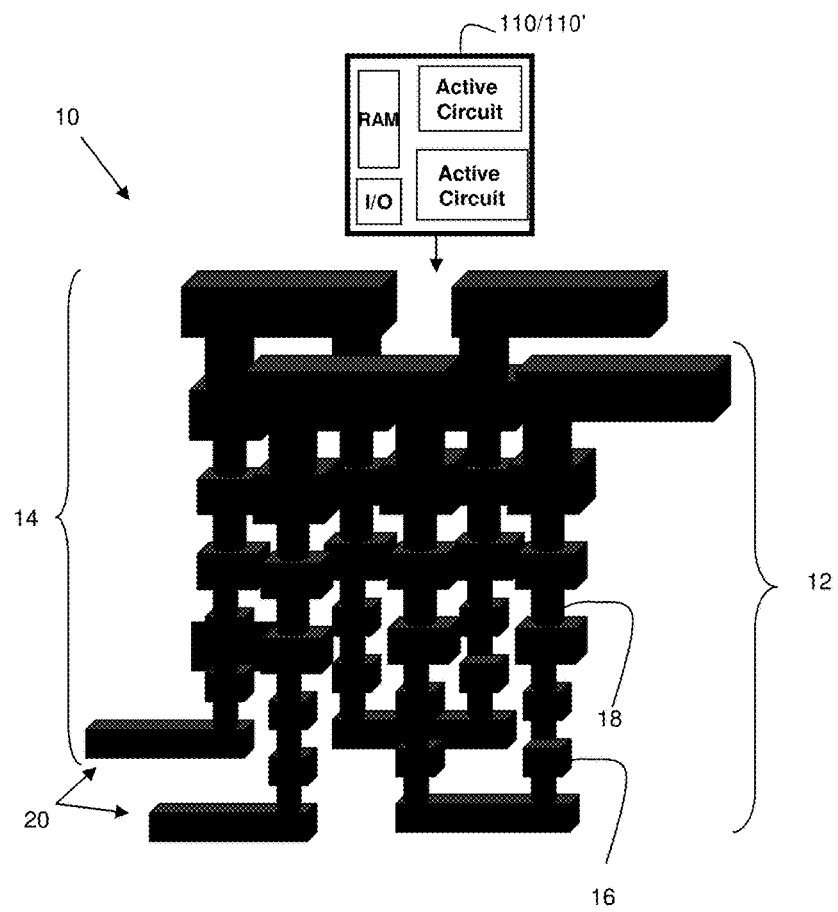
FIG. 1 shows a moisture detection circuit and methods of manufacturing, in accordance with aspects of the present invention.

FIG. 1 shows a double or triple wall edge seal with capacitance measurement circuit and methods of manufacturing, in accordance with aspects of the present invention. In embodiments, the double or triple wall edge seal with capacitance measurement circuit 10 includes a plurality of wiring structures 12, 14 comprising a plurality of wiring levels 16 connected by via interconnect structures 18. The plurality of wiring structures 12, 14 can be, e.g., guardring and/or crackstop structures located adjacent an edge of a chip.

As in any of the embodiments, the guardring and/or crackstop structures can be the same structures, positioned at different locations around one or more active devices, which are structured to prevent cracking and moisture penetration. In further embodiments, the guardring and/or crackstop structures can be interchangeable with one another. Also, as should be understood by one of skill in the art, the guardring and/or crackstop structures are metal structures (e.g., ring structures) surrounding one or more active devices within an integrated circuit. As in any of the embodiments, the guardring and/or crackstop structures completely surround the one or more devices of an integrated circuit thereby providing chip moisture detection and moisture ingression monitoring both vertically and horizontally at any metal levels, in 360 degrees.

In embodiments, the wiring levels 16 and via interconnect structures 18 are metal structures embedded within dielectric material, e.g., interlevel dielectric material. The metal structures can be composed of any metal material used in integrated circuit fabrication processes, e.g., CMOS processes. By way of illustrative example, the wiring levels 16 can be copper or aluminum; whereas, the via interconnect structures 18 can be tungsten, copper or aluminum.

Still referring to FIG. 1, the wiring structures 12, 14 include a moisture detection circuit 20. In embodiments, the moisture detection circuit 20 can be composed of two electrodes on different wiring levels, which are separated by an air gap or other material which allows moisture detection between two electrodes forming the moisture detection circuit 20. The electrodes form a capacitor which is composed of metal materials such as, e.g., copper or aluminum, fabricated with the wiring structures 12, 14. It should be understood by those of skill in the art that the moisture detection circuit 20 can be provided at any wiring level. An active circuit 110/110' is placed inside structure 10 and therefore is protected from moisture and oxygen by the structure 10. Moisture detection circuit 20 with electrical communication to the electrodes of structure 10 is part of active circuit 110/110'. The active circuit includes RAM, I/O and other active circuitry to monitor, detect and notify a user of moisture ingression, as further described with respect to FIGS. 5 and 6.

In embodiments, the wiring levels 16, via interconnect structures 18 and moisture detection circuit 20 can be fabricated using conventional back end of the line (BEOL) processes including lithography, etching and deposition processes. For example, at each wiring layer, a resist can be formed on an insulator layer (interlevel dielectric layer) which is then exposed to energy (light) to form a pattern. A reactive ion etching (RIE) is performed through the pattern to form an opening which corresponds to the shape and size of each of the wiring levels 16, via interconnect structures 18 and moisture detection circuit 20. The resist can then be stripped using conventional processes such as oxygen ashing or other stripants. A metal material, e.g., metal or metal alloy or combinations thereof, is deposited within the opening using conventional deposition methods such as, for example, chemical vapor deposition (CVD), plasma enhanced CVD (PECVD), etc.

After each of the metal deposition steps, the structure can undergo a planarization process, prior to the deposition of a next interlevel dielectric layer. The planarization process can comprise a chemical mechanical polishing step in order to remove any excess metal on a surface of the interlevel dielectric layer. In embodiments, the interlevel dielectric layer can be an oxide material deposited in a low temperature oxide CVD process. The interlevel dielectric layer can also be a low-k dielectric material and, in embodiments, the interlevel dielectric layer can be removed between the metal structures of the moisture detection circuit by an etching process.

In embodiments, the moisture detection circuit 20 can be electrically connected to an active circuit 110/110' which detects and notifies a user of moisture ingression. In more specific embodiments, the moisture detection circuit 20 can be a capacitor, e.g., two metal plates with insulator material therebetween. In even more specific embodiments, the detection circuit 20 can be a Cu/low-k MIM (metal-insulator-metal) capacitor structure; although other metal materials are also contemplated by the present invention. In still further embodiments, the MIM capacitor can include an airgap between the opposing metal structures, with the airgap being formed by an etching or removal of the insulator material during the above noted steps.

As a basic operation principle of the moisture detection circuit 20, capacitance of the capacitor increases as moisture level increases. For example, using equation 1 below, $$V_C = \frac{I * t}{C} \qquad (1)$$

where "Vc" is the voltage across the capacitor, "I" is the constant charge current, "t" is the charge time and "C" is the capacitance, Vc will decrease due to moisture ingression, e.g., with moisture level increasing. As should be understood, Vc will decrease because (i) moisture increases the effective k value and (ii) capacitor is more leaky due to enhanced conduction.

Figure 2:
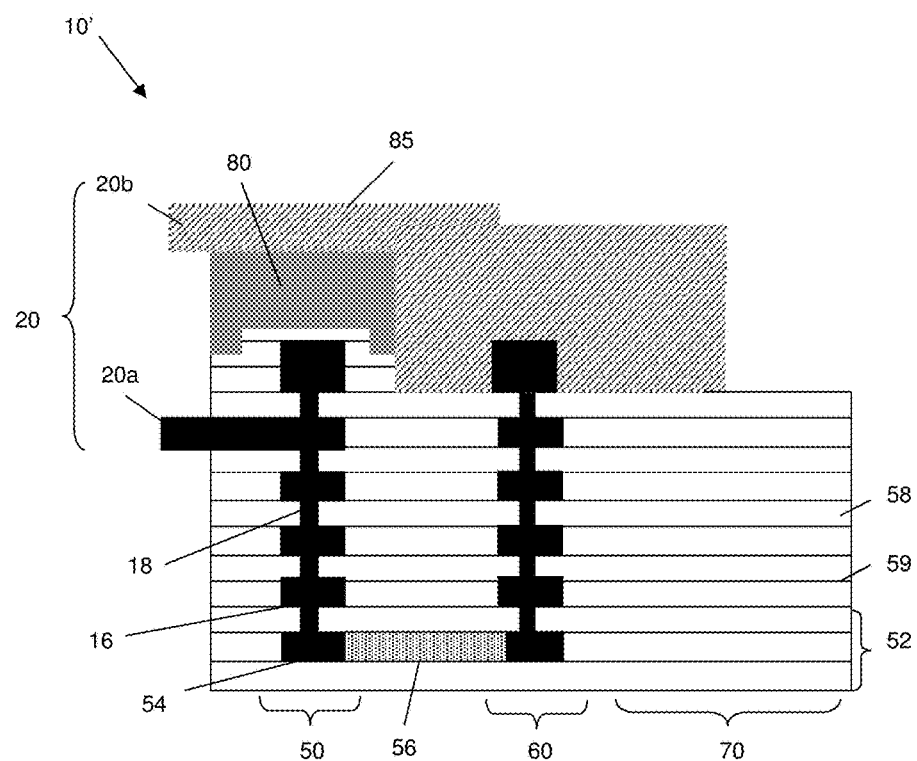
FIG. 2 shows a moisture detection circuit and methods of manufacturing, in accordance with additional aspects of the present invention.

FIG. 2 shows a moisture detection circuit and methods of manufacturing, in accordance with aspects of the present invention. In more specific embodiments, the moisture detection circuit comprises a guardring sensor with C4 wire. More specifically, the structure 10' shown in FIG. 2 includes a guardring structure 50 and a crackstop structure 60, adjacent to a scribe line 70. The structure 10' further includes a substrate 52 which can include one or more devices 54 separated by shallow trench isolation structures 56. In the embodiments, the substrate 52 can be a silicon-on-insulator substrate (SOI), as an example; although other substrates are also contemplated by the present invention, e.g., silicon on bulk wafers. The one or more devices 54 can include any devices such as, e.g., transistors, diodes, etc., separated by the shallow trench isolation structures 56. The one or more devices 54 and shallow trench isolation structures 56 can be fabricated by conventional CMOS fabrication processes such that no further explanation is required for one of ordinary skill in the art to understand the invention.

Still referring to FIG. 2, the guardring structure 50 and crackstop structure 60 include a plurality of layers comprising the wiring levels 16 and via interconnect structures 18 as already described herein, formed within insulator material 58 (e.g., interlevel dielectric material such as SiCoH or SiO$_2$). In embodiments, each insulator layer 58 in the back end of the line (BEOL) can be separated by a capping material 59, e.g., nitride, SiN$_2$, SiC or SiCN$_2$, formed using conventional deposition processes, e.g., CVD.

In embodiments, the detection circuit 20 can include a two terminal capacitor comprising electrodes 20a and 20b. In embodiments, the electrode 20a can be formed from the guardring structure 50, at a certain level of the wiring layers. For example, as shown in FIG. 2, the electrode 20a can be formed on the fourth wiring layer; although other wiring layers are contemplated by the present invention. On the other hand, the electrode 20b can be formed from a solder bump, e.g., C4 solder bump, or Ball Limiting Metallurgy (BLM) 85 formed on a polyimide material 80, in electrical contact with a metal wiring layer. The solder bump 85 can be tin, for example. The electrodes 20a and 20b will be biased to ground and to an active circuit as described herein. Also, in embodiments, the electrode 20a can be exposed by an etching process or, more preferably, during a cleavage or cutting process which dices the chips.

Figure 3:
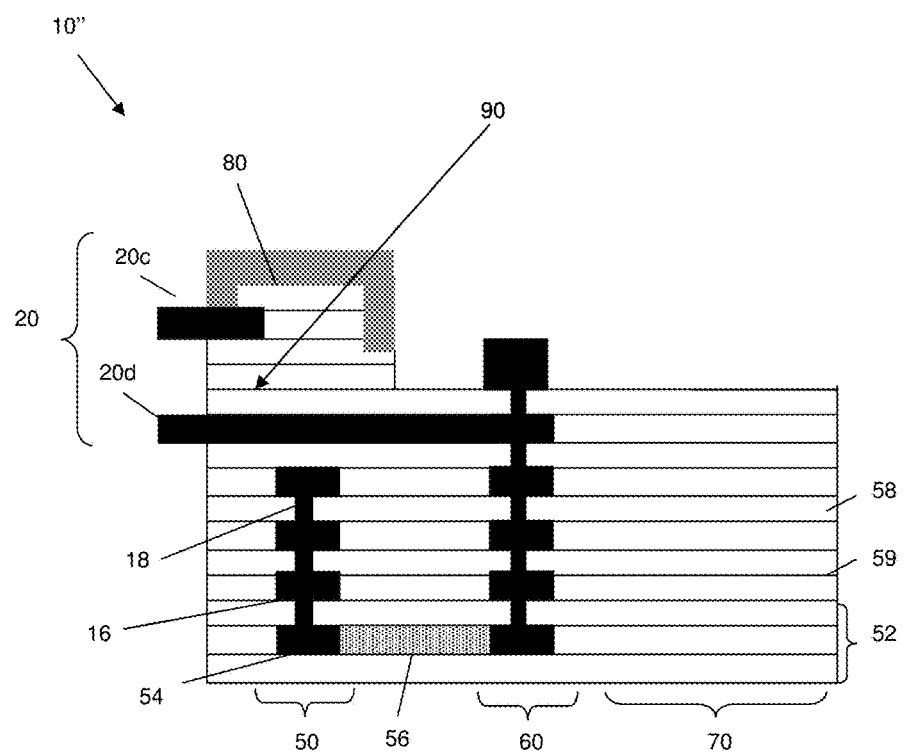
FIG. 3 shows a moisture detection circuit and methods of manufacturing, in accordance with additional aspects of the present invention.

FIG. 3 shows a moisture detection circuit and methods of manufacturing, in accordance with aspects of the present invention. In more specific embodiments, the moisture detection circuit comprises a guardring sensor with gap for a wire. In the structure 10" of FIG. 3, the detection circuit 20 includes a two terminal capacitor comprising electrodes 20d and 20c. The electrodes 20d and 20c will be biased to ground and to an active circuit as described herein.

In embodiments, the electrode 20d can be formed from the crackstop structure 60, at a certain level of the wiring layers as already described herein. For example, as shown in FIG. 3, the electrode 20d can be formed on the fourth wiring layer; although other wiring layers are contemplated by the present invention. In this and other embodiments, the electrode 20d can be also formed from the guardring structure 50, assuming a gap is large enough to accommodate the electrode 20c, at a certain level of the wiring layers as already described herein.

On the other hand, as shown in FIG. 3, the electrode 20c can be formed in an upper insulator layer 58, above the electrode 20d. The electrode 20c can be formed from any metal material and preferably the same metal material as the electrode 20d, using similar lithography, etching and deposition processes as described herein. In embodiments, a gap 90 is formed in the structure 10" to accommodate the formation and placement of the electrode 20c.

Still referring to FIG. 3, the structure 10" includes the guardring structure 50 and the crackstop structure 60, adjacent to the scribe line 70, as already described with respect to FIG. 2. For example, the guardring structure 50 and the crackstop structure 60 are formed within insulator material 58 (e.g., interlevel dielectric material such as SiCoH or SiO$_2$), with each insulator layer 58 in the back end of the line (BEOL) being separated by a capping material 59, e.g., nitride, SiN$_2$, SiC or SiCN$_2$, formed using conventional deposition processes. The structure 10" further includes a substrate 52, e.g., SOI, which can include one or more devices 54 separated by shallow trench isolation structures 56. The one or more devices 54 can include any devices such as, e.g., transistors, diodes, etc., separated by the shallow trench isolation structures 56, fabricated by conventional CMOS fabrication processes.

Figure 4:
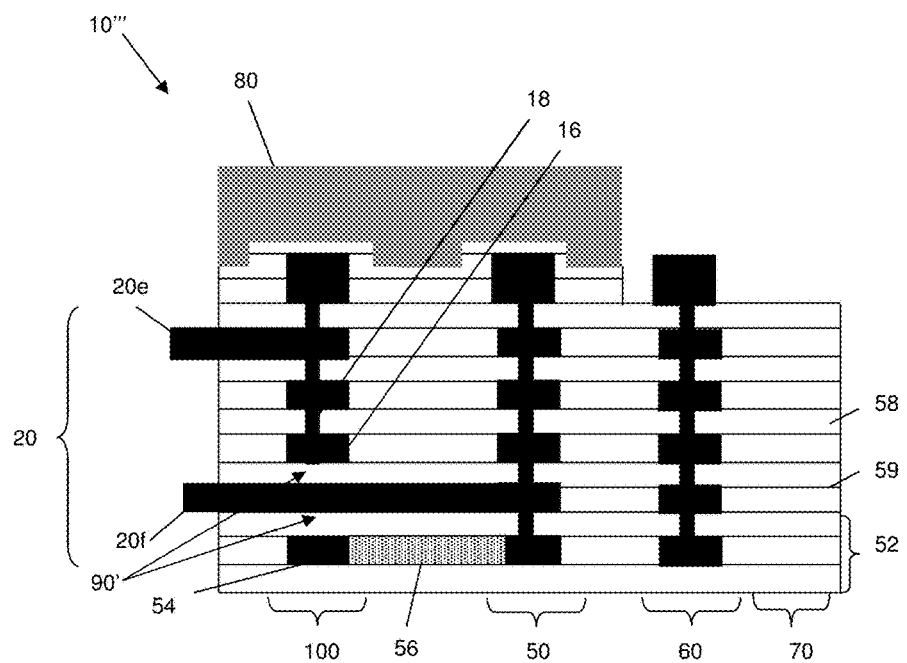
FIG. 4 shows a moisture detection circuit and methods of manufacturing, in accordance with additional aspects of the present invention.

FIG. 4 shows a moisture detection circuit and methods of manufacturing, in accordance with additional aspects of the present invention. In more specific embodiments, the moisture detection circuit comprises a guardring as one plate of a sensor. In the structure 10''' of FIG. 4, the detection circuit 20 includes a two terminal capacitor comprising electrodes 20e and 20f. The electrodes 20e and 20f will be biased to ground and to an active circuit as described herein.

In embodiments, the electrode 20e can be formed from a capacitor plate 100, at a certain level of the wiring layers as already described herein. For example, as shown in FIG. 4, the electrode 20e can be formed on the fourth wiring layer; although other wiring layers are contemplated by the present invention. On the other hand, as shown in FIG. 4, the electrode 20f can be formed below the electrode 20e, extending from the guardring structure 50. The electrode 20f can be formed from any metal material and preferably the same metal material as the electrode 20e and other wiring levels 16, using similar lithography, etching and deposition processes as described herein. In embodiments, a gap 90' is formed in the structure 10''' to accommodate the formation and placement of the electrodes 20e and 20f.

Still referring to FIG. 4, the structure 10''' includes the capacitor plate 100, the guardring structure 50 and the crackstop structure 60, adjacent to the scribe line 70. Similar to the formation of the guardring structure 50 and the crackstop structure 60 as already described with respect to FIGS. 2 and 3, the capacitor plate 100 comprises a plurality of wiring levels 16 connected to the via interconnect structures 14. As with the guardring structure 50 and the crackstop structure 60, the plurality of wiring levels 16 and the via interconnect structures 14 are formed within insulator material 58 (e.g., interlevel dielectric material such as SiCoH or SiO$_2$), which each insulator layer 58 in the back end of the line (BEOL) being separated by a capping material 59, e.g., nitride, SiN$_2$, SiC or SiCN$_2$, formed using conventional deposition processes. In embodiments, the guardring structure 50, the crackstop structure 60 and the capacitor plate 100 can be formed in the same processing steps, similar to that already described.

The structure 10''' further includes a substrate 52 (e.g., SOI) which can include one or more devices 54 separated by shallow trench isolation structures 56. The one or more devices 54 can include any devices such as, e.g., transistors, diodes, etc., separated by the shallow trench isolation structures 56, fabricated by conventional CMOS fabrication processes.

Figure 5:
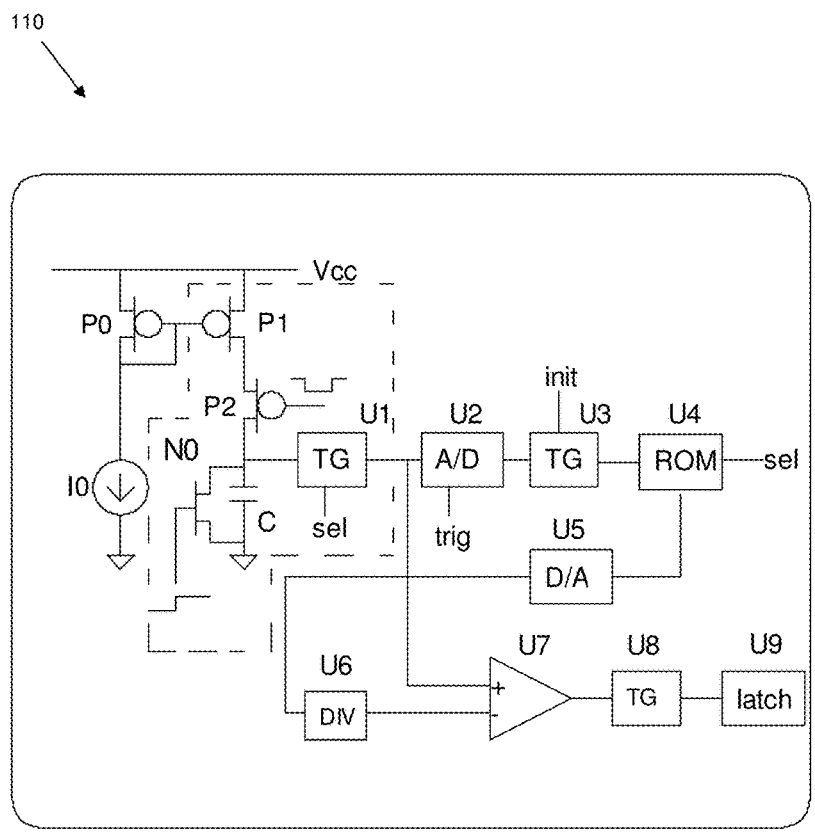
FIG. 5 shows a detector circuit with initial reference, in accordance with aspects of the present invention.

FIG. 5 shows a detector circuit with initial reference, in accordance with aspects of the present invention. More specifically, the detector circuit 110 includes the following components: (i) P0, P1: PFETS; (ii) P2: switching PFET; (iii) I0: reference current source; (iv) C: active moisture sensor (e.g., MIM capacitor); (v) N0: discharge NFET; (vi) TG: transmission gate; (vii) A/D: analog to digital converter; (viii) ROM: read only memory; (ix) D/A: digital to analog converter; (x) DIV: voltage divider; (xi) U7: voltage comparator; (xii) Sel: address select line; and (xiii) Trig: A/D sample trigger.

In embodiments, a chip can include a plurality of the moisture detectors as described herein, noting that P1, P2, N0, C and U1 form one moisture test unit and all of the units would share the remaining components. In embodiments, each test unit would be assigned an address in the on chip ROM, U4.

At an initial value of Vc, during chip power on for the first time, it is assumed that no moisture is in the chip. The measured value of Vc, at power on, is converted to digital format by the A/D converter and saved in ROM as the initial value. The operation procedures for the first time of power on comprises:

1. The positive pulse on the gate of NFET N0 turns on N0 and discharges the MIM capacitor C completely.

2. The negative pulse of the pulse width T turns on P2, and the capacitor C is charged by the current I0 for the time period of T.

3. The signal "sel" turns on U1 and the signal "trig" triggers U2 which samples the voltage Vc and saves the digital initial value in U4 when the first time of powered on and the signal "init" is active.

4. The initial digital value is converted by the DAC U5 to the threshold analog voltage of the voltage comparator U7 for the real time moisture detection through the voltage divider U6, which provides a margin for the voltage comparison.

The detector circuit 110 is also used in real time operation as described herein. For example, operation procedures for real time operation comprises:

1. The positive pulse on the gate of NFET N0 turns on N0 and discharges the MIM capacitor C completely.

2. The negative pulse of the pulse width T turns on P2, and the capacitor C is charged by the current I0 for the time period of T.

3. If the value of Vc is higher than the threshold voltage, the output of U7 is at logic high and is thus normal. However, if Vc is lower than the threshold voltage, the output of U7 is at the logic low, the latch U9 is triggered through U8 and an alarm will be sent out.

Figure 6:
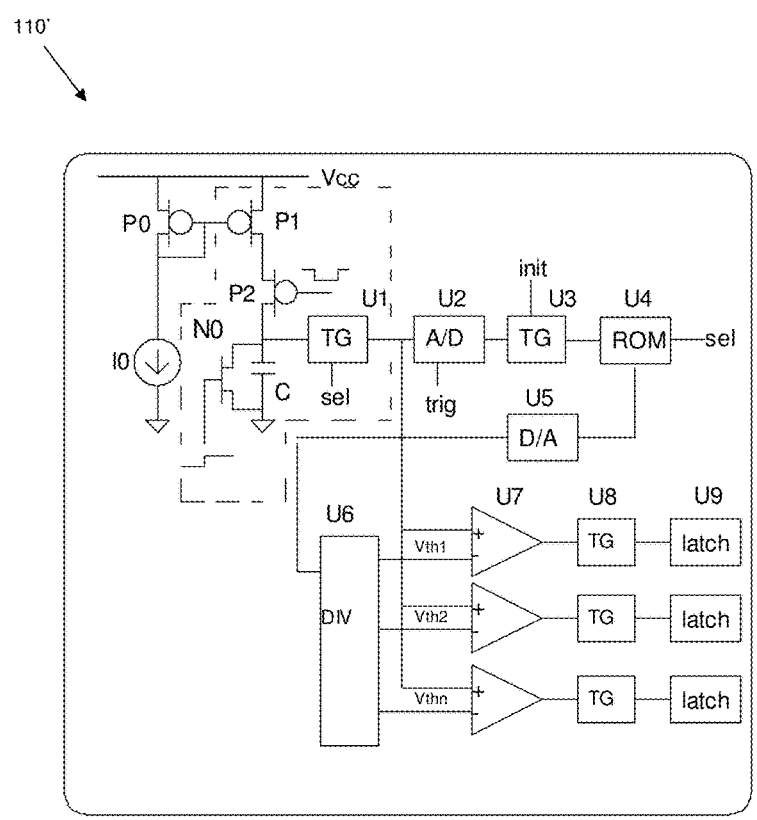
FIG. 6 shows a detector circuit with multiple levels of warning, in accordance with aspects of the present invention.

FIG. 6 shows a detector circuit with multiple levels of warning, in accordance with aspects of the present invention. The detector circuit 110' shown in FIG. 6 is similar to that in FIG. 5, with the difference that the voltage divide U6 provides multiple threshold voltages for a set of voltage comparators so that the multiple warnings of the moisture levels can be implemented.

Accordingly, by implementing the circuits described herein, moisture spread, speed detection and residual lifetime warnings can be provided. Moreover, since the crackstop/guarding could comprise multiple stacked via-line walls, e.g., wiring levels and via interconnects, the moisture detection units (e.g., capacitors) can be divided into multiple detectors (units) with two adjacent walls but at different positions. The time difference of the moisture detected at the different detectors can be counted as the moisture spread/ingression speed. Therefore, a time dependent moisture ingression status could be quantitatively calculated and the residual lifetime of moisture ingression to reach critical circuit components could be estimated.

The method(s) as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A method comprising:
   forming a guardring structure and a crackstop structure extending vertically through an edge of the chip;
   forming at least one electrode electrically connected to either the guardring structure or the crackstop structure; and
   forming a second electrode connected to the at least one electrode to form a capacitor with the at least one electrode,
   wherein the guardring structure and the crackstop structure are formed from metal features extending vertically through multiple wiring layers and insulator layers along the edge of the chip.

2. The method of claim 1, further comprising forming a moisture detection circuit which is connected to the at least one electrode and the second electrode of the capacitor.

3. The method of claim 2, wherein the at least one electrode and the second electrode of the capacitor are formed to be biased to ground and to the moisture detection circuit.

4. The method of claim 1, wherein the guardring and the crackstop structure are formed at different locations around one or more active devices.

5. The method of claim 4, wherein the guardring and the crackstop structure completely surround the one or more active devices providing chip moisture detection and moisture ingression monitoring both vertically and horizontally at any metal level, in 360 degrees.

6. The method of claim 1, wherein the at least one electrode is formed from the guardring ring extending from a predetermined wiring layer and the second electrode forming the capacitor is formed from a solder bump or ball limiting metallurgy.

7. The method of claim 1, wherein the at least one electrode is formed from the crackstop structure extending from a predetermined wiring layer and the second electrode is formed separated therefrom by a gap formed between the one electrode and the second electrode.

8. The method of claim 1, wherein the at least one electrode is formed from the crackstop structure extending from a predetermined wiring layer and the second electrode is extending from a capacitor plate, which is separated therefrom by a gap formed between the one electrode and the second electrode.

9. A method comprising:
   forming a guardring structure and a crackstop structure extending vertically through an edge of the chip;
   forming at least one electrode electrically connected to either the guardring structure or the crackstop structure; and
   forming a second electrode connected to the at least one electrode to form a capacitor with the at least one electrode, wherein the guardring structure and the crackstop structure are formed from a plurality of metal layers comprising wiring and via interconnect structures within insulator material.

* * * * *